United States Patent
Zilberman

(10) Patent No.: US 8,651,867 B2
(45) Date of Patent: *Feb. 18, 2014

(54) DENTAL CROWNS

(75) Inventor: Uri Zilberman, Nes Ziona (IL)

(73) Assignee: Uri-Dent Ltd., Ashkelon (IL)

( * ) Notice: Subject to any disclaimer, the term of this patent is extended or adjusted under 35 U.S.C. 154(b) by 643 days.

This patent is subject to a terminal disclaimer.

(21) Appl. No.: 10/685,803

(22) Filed: Oct. 16, 2003

(65) Prior Publication Data

US 2004/0115592 A1 Jun. 17, 2004

Related U.S. Application Data

(63) Continuation-in-part of application No. PCT/IL02/00310, filed on Apr. 16, 2002, which is a continuation of application No. 09/903,096, filed on Jul. 11, 2001, now Pat. No. 6,592,373.

(30) Foreign Application Priority Data

Apr. 17, 2001 (IL) .......................................... 142657

(51) Int. Cl.
A61C 5/08 (2006.01)
(52) U.S. Cl.
USPC ....................................................... 433/218
(58) Field of Classification Search
USPC ................... 433/218, 219, 222.1, 223, 212.1
See application file for complete search history.

(56) References Cited

U.S. PATENT DOCUMENTS

| | | | | | |
|---|---|---|---|---|---|
| 3,585,723 | A | * | 6/1971 | Simor | 433/219 |
| 3,647,498 | A | * | 3/1972 | Dougherty | 427/2.26 |
| 4,015,332 | A | | 4/1977 | Manne | |
| 4,129,946 | A | * | 12/1978 | Kennedy | 433/37 |
| 4,215,033 | A | | 7/1980 | Bowen | |
| 4,300,886 | A | * | 11/1981 | Suling et al. | 523/115 |
| 4,381,918 | A | | 5/1983 | Ehrnford | |
| 4,433,959 | A | | 2/1984 | Faunce | |
| 4,678,435 | A | * | 7/1987 | Long | 433/218 |
| 5,332,390 | A | | 7/1994 | Rosellini | |
| 5,346,397 | A | | 9/1994 | Braiman | |
| 5,487,663 | A | * | 1/1996 | Wilson | 433/218 |

(Continued)

FOREIGN PATENT DOCUMENTS

| | | |
|---|---|---|
| EP | 0 030 850 | 6/1981 |
| GB | 639700 | 7/1950 |

(Continued)

OTHER PUBLICATIONS

Zilberman, U., "The new generation of pre-fabricated tooth-colored crowns for children". 18th Congress of the International Associates of Paediatric Dentistry, article No. S016-4, 12-15, Sep. 2001 (Abstract).

(Continued)

*Primary Examiner* — Robyn Doan
*Assistant Examiner* — Matthew Nelson
(74) *Attorney, Agent, or Firm* — Vorys, Sater, Seymour and Pease LLP; Susanne M. Hopkins; William L. Klima

(57) ABSTRACT

The present invention provides a dental crown formed of a thermoplastic polymer material, the crown comprising: a tooth shaped top surface; and flexible side surfaces, at least one of which includes an inwardly directed bottom portion.

10 Claims, 4 Drawing Sheets

(56) References Cited

U.S. PATENT DOCUMENTS

| | | | |
|---|---|---|---|
| 5,552,390 A | 9/1996 | Scholar et al. | |
| 5,624,261 A | 4/1997 | Wiedenfeld | |
| 5,672,305 A | 9/1997 | Kogure | |
| 5,709,548 A | 1/1998 | Oxman et al. | |
| 5,730,926 A | 3/1998 | Matsumoto et al. | |
| 5,951,294 A * | 9/1999 | Pierson | 433/218 |
| 6,068,481 A * | 5/2000 | Worthington | 433/219 |
| 6,106,295 A | 8/2000 | Wilson | |
| 6,186,790 B1 * | 2/2001 | Karmaker et al. | 433/215 |
| 6,257,892 B1 * | 7/2001 | Worthington | 433/219 |
| 6,592,373 B2 | 7/2003 | Zilberman | |

FOREIGN PATENT DOCUMENTS

| | | |
|---|---|---|
| JP | 1256949 | 10/1989 |
| JP | 07-088121 | 4/1995 |
| JP | 3050848 | 5/1998 |
| JP | 11-262947 | 9/1999 |
| JP | 11-216148 | 10/1999 |
| RU | 1814543 A3 | 5/1993 |
| WO | 99/17676 | 4/1999 |

OTHER PUBLICATIONS

"Dental D Acetal Resin" 9/98 product brochure, Quattro Ti S.r.l., Tecnopolimeri Biomediali.

* cited by examiner

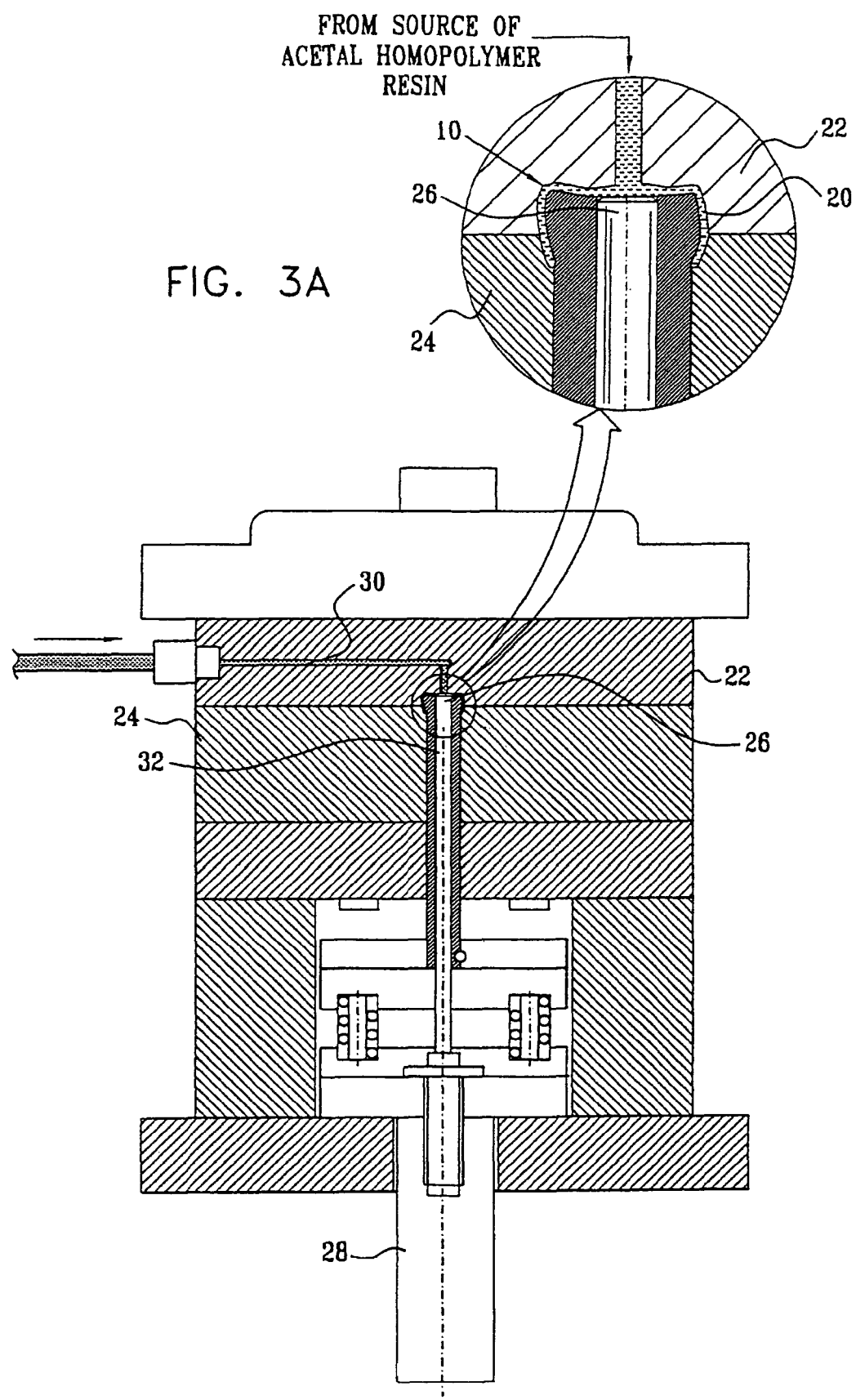

DENTAL CROWNS

FIELD OF THE INVENTION

The present invention relates to tooth prostheses generally and more particularly to crowns.

BACKGROUND OF THE INVENTION

The following U.S. Patents and publications are believed to represent the current state of the art: U.S. Pat. Nos. 4,129,946; 5,487,663; 5,624,261; 5,709,548; 6,106,295.

SUMMARY OF THE INVENTION

The present invention seeks to provide a mass-produced, tooth colored pre-fabricated crown, particularly useful in pediatric dentistry for treatment of primary teeth and permanent molars having extensive carious lesions.

There is thus provided by the present invention a dental crown formed of a thermoplastic polymer material, said crown comprising:
 a tooth shaped top surface; and
 flexible side surfaces, at least one of which includes inwardly directed bottom portion.

In other words, at least one of the side surfaces defines an undercut.

The term "undercut" is used herein to indicate that the diameter of the outlet of the crown is reduced in comparison to the maximal internal diameter of the crown.

According to a preferred embodiment of the invention, the thermoplastic polymer material comprises a polymer selected from the following polymers: polyacetal, polyacrylate, polymethylmethacrylate (PMMA), polyamide, polyaryletherketone (PAEK), polyetherketone (PEK), polyetheretherketone (PEEK), polyetherimide (PEI), polyethersulfone (PES), polysulfone (PSU), and mixtures thereof. More preferably, the thermoplastic polymer is a homo- or co-polymer of acetal resin, polyetheretherketone (PEEK) or polymethylmethacrylate (PMMA).

According to another preferred embodiment of the invention, the thermoplastic polymer material further comprises at least one of the following: fibers, fillers, pigments and reinforcements. The fibers and fillers may be in their conventional or nano size.

A dental crown according to the present invention may be formed by several methods. Non-limiting examples of such methods includes injection molding, compression molding and machining.

According to a preferred embodiment of the invention, the dental crown is produced by mass production injection molding which comprises:
 providing a multi-element mold; and
 employing the multi-element mold to injection mold a dental crown from a thermoplastic polymer material.

Preferably, the multi-element mold includes an ejector, which is being operated to eject the molded crown following opening the multi-element mold.

BRIEF DESCRIPTION OF THE DRAWINGS

The present invention will be understood and appreciated more fully from the following detailed description, taken in conjunction with the drawings in which:

FIGS. 3A, 3B and 3C illustrate the operation of an apparatus for manufacturing a dental crown from acetal homopolymer resin in accordance with a preferred embodiment of the present invention.

DETAILED DESCRIPTION OF THE INVENTION

Figure 1:
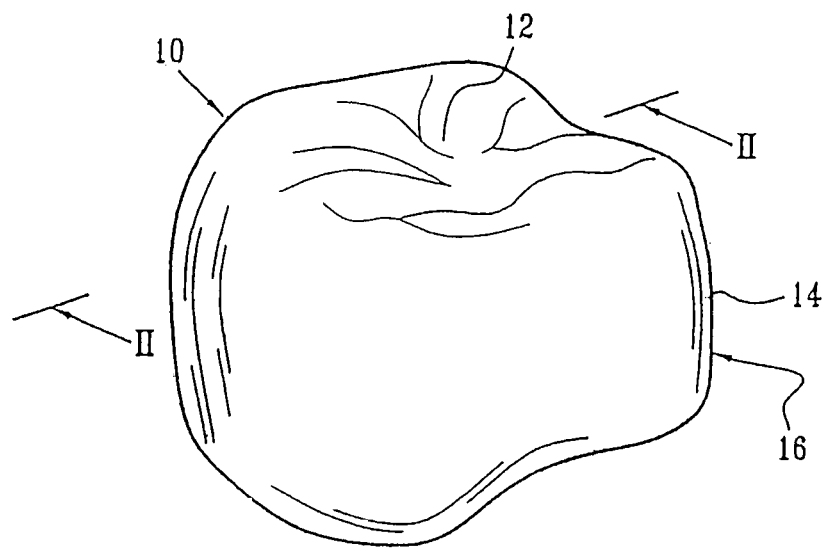
FIG. 1 is a simplified pictorial illustration of a dental crown formed of acetal homopolymer.
Figure 2:
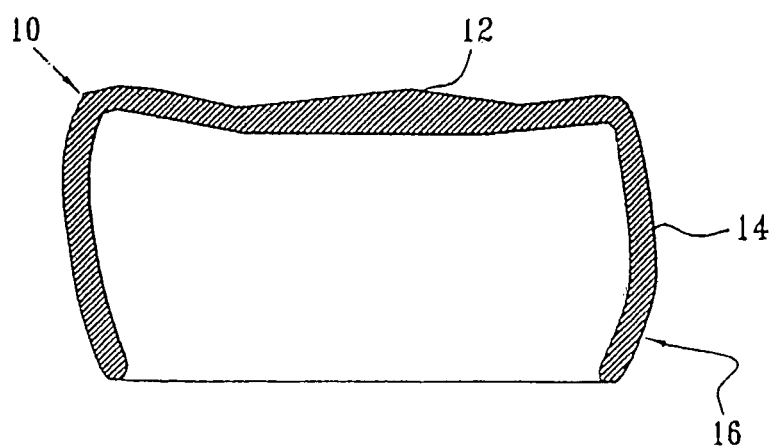
FIG. 2 is a sectional illustration of the dental crown of FIG. 1, taken along lines II-II in FIG. 1.

Reference is now made to FIG. 1, which is a simplified pictorial illustration of a dental crown formed of acetal homopolymer resin and to FIG. 2, which is a sectional illustration of the dental crown of FIG. 1, taken along lines II-II in FIG. 1.

As seen in FIGS. 1 and 2, there is provided in accordance with a preferred embodiment of the present invention an injection molded dental crown 10 formed of an acetal homopolymer resin. A preferred material for the crown is acetal homopolymer resin (DELRIN®) which is commercially available from DuPont.

As can be readily seen in FIGS. 1 and 2, the dental crown 10 is formed with a generally conventionally tooth shaped top surface 12 and depending side surfaces 14 at least one of which defines an undercut 16. Preferably, the depending side surfaces 14 are flexible. Crown 10 may readily be mounted, by conventional methods, such as through the use of dental cement in the mouth of a patient, typically a child, as part of treatment of primary teeth and permanent molars having extensive carious lesions. It is a particular feature of the invention that crown 10 is of a color which generally matches that of the patient's teeth.

The crown of the present invention is characterized by high tensile strength, high impact resistance and stiffness, excellent fatigue endurance and resistance to moisture, excellent dimensional stability and sufficient resilience and resistance to creep. It has the natural appearance of a vital tooth.

Figure 3B:
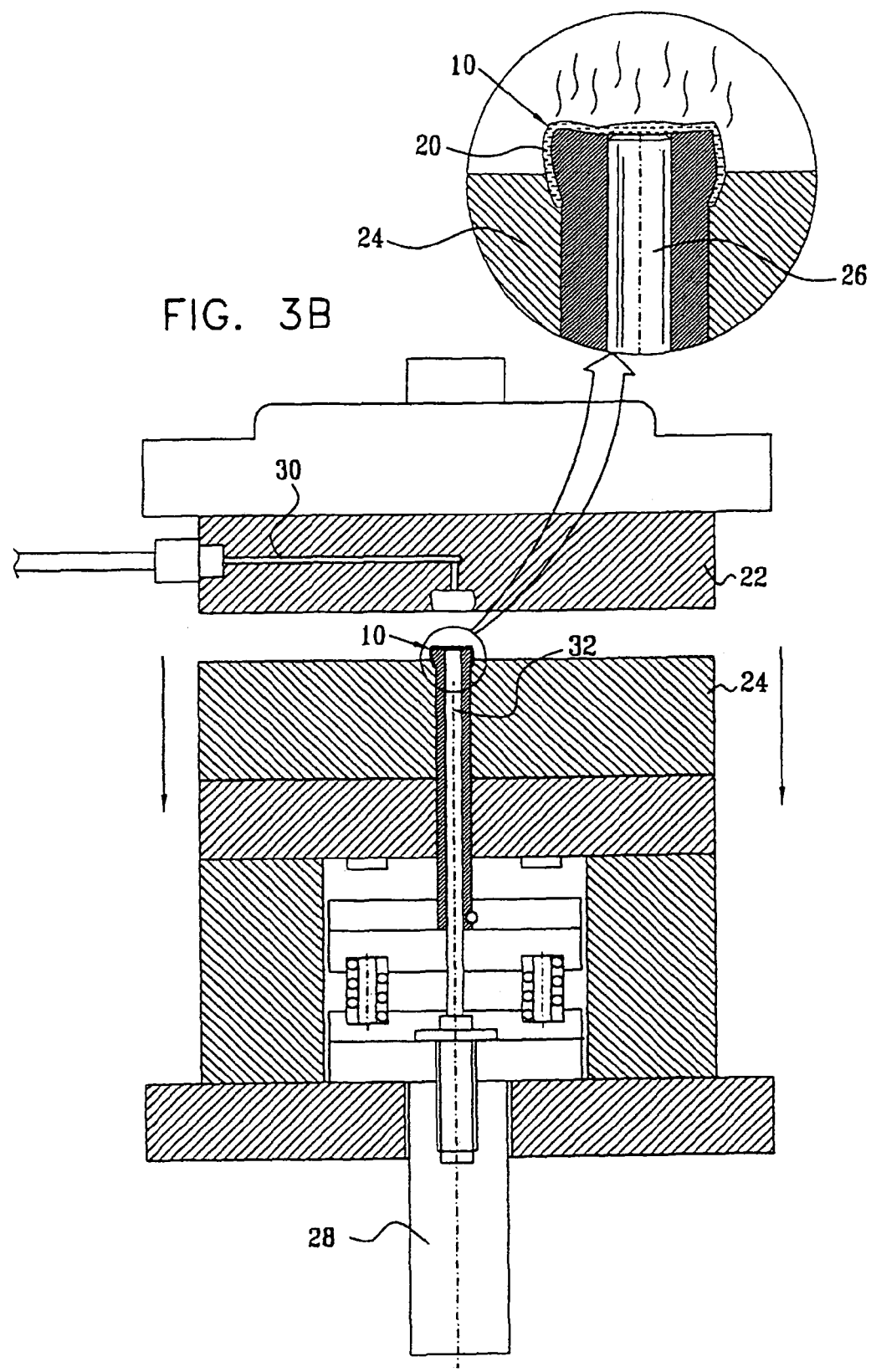
Figure 3C:
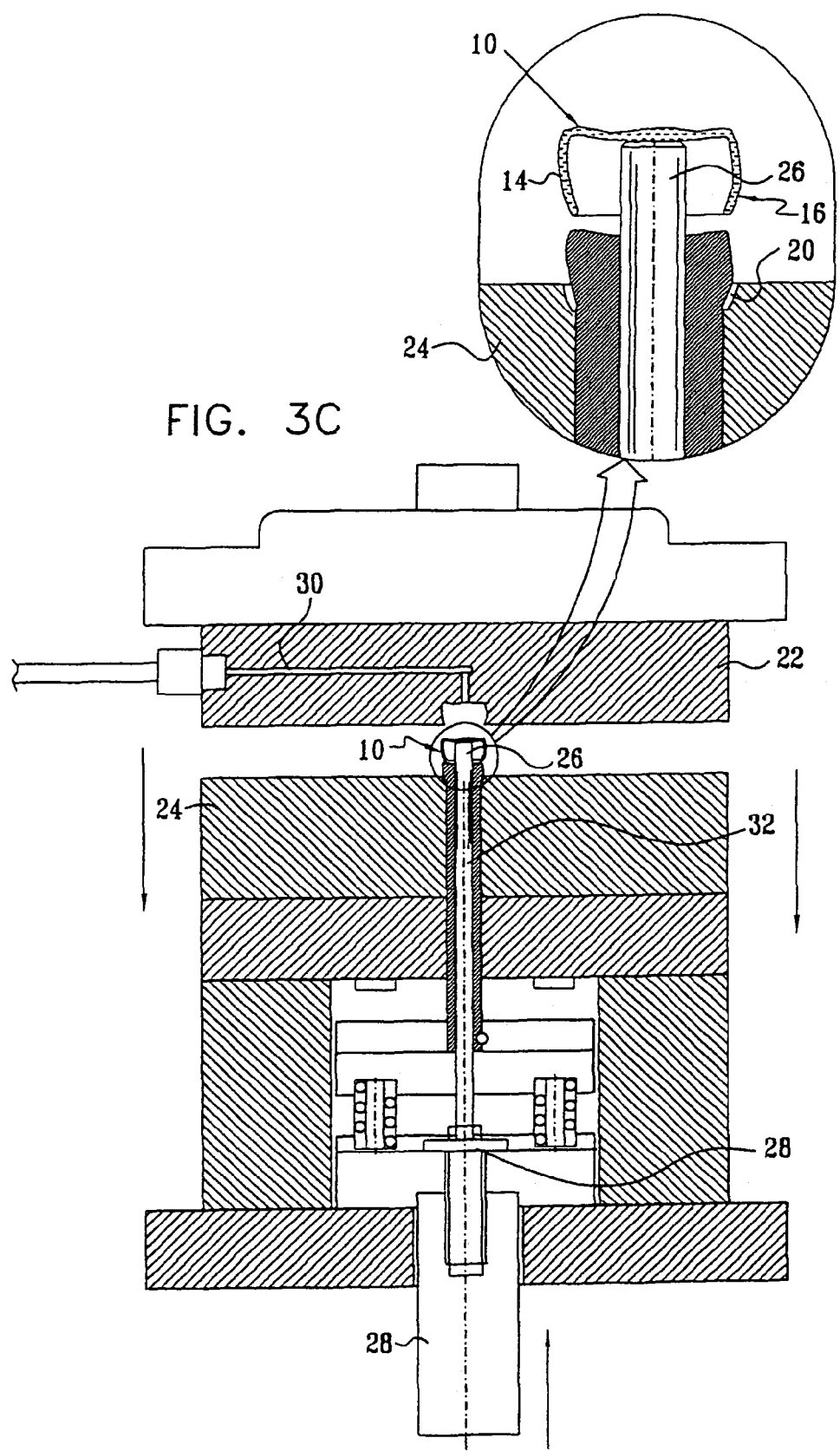

Reference is now made to FIGS. 3A, 3B and 3C, which illustrate the operation of an apparatus for manufacturing a dental crown from acetal homopolymer resin in accordance with a preferred embodiment of the present invention.

As seen in FIGS. 3A, 3B and 3C, the crown 10 is molded in a mold cavity 20 which is defined by a top mold element 22, a bottom mold element 24 and an ejector 26. The ejector 26 forms part of an internal mold element 32.

FIG. 3A shows the stage of molding when the top mold element 22 lies in tight engagement with the bottom mold element 24 and the ejector 26. The dental crown 10, which is fabricated on the ejector 26, is formed by the injection of acetal homnpolymer resin material from a source of acetal homopolymer resin (not shown) into the mold cavity 20, via a channel 30 cut in the top mold element 22.

FIG. 3B shows an initial release stage wherein the bottom mold element 24 is separated from the top mold element 22, thus permitting removal of the molded crown 10 from cavity 20.

FIG. 3C shows an ejection stage wherein ejector 26, driven by a piston 28 moves upwardly relative to bottom mold element 24 and pushes crown 10 out of cavity 20. Due to the resilience of the depending side surfaces 14, the action of the ejector 26 is able to disengage the internal mold element 32 from the crown 10 notwithstanding the presence of undercut 16.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

The invention claimed is:

1. A dental crown configured to be readily mountable in a patient's mouth as part of a treatment of primary teeth and permanent molars, the dental crown having a natural appearance and color of a vital tooth and consisting of:
   a thermoplastic material layer configured to define a tooth shaped top surface; and
   depending flexible side surfaces extending continuously from said tooth shaped top surface towards a bottom portion of the dental crown, said thermoplastic material layer being configured to enable dimensional stability and sufficient resilience of the crown, and
   a bottom portion of at least one of said depending flexible continuous side surfaces comprising an undercut defining an inwardly directed inner surface of said bottom portion, the resilience of the flexible depending side surfaces and the undercut made in the bottom portion of at least one of the flexible side surfaces, enabling the dental crown to be directly mounted on a primary tooth or permanent molar.

2. A dental crown according to claim 1, wherein said thermoplastic material comprises a polymer selected from polyacetal, polyacrylate, polymethylmethacrylate (PMMA), polyamide, polyaryletherketone (PAEK), polyetherketone (PEK), polyetheretherketone (PEEK), polyetherimide (PEI), polyethersulfone (PES), polysulfone (PSU), and mixtures thereof.

3. A dental crown according to claim 2, wherein said polymer is a homo- or co-polymer of acetal resin, polyetheretherketone (PEEK) or polymethylmethacrylate (PMMA).

4. A dental crown according to claim 1, wherein said thermoplastic material comprises at least one of the following: fibers, fillers, pigments and reinforcements.

5. A dental crown according to claim 1, formed by injection molding.

6. A dental crown according to claim 5, produced by a mass production injection molding method, said mass production injection molding method comprising:
   providing a multi-element mold; and
   employing the multi-element mold to injection mold a dental crown from a thermoplastic polymer material.

7. A dental crown according to claim 6, wherein said multi-element mold includes an ejector, which is being operated to eject the molded crown following opening the multi-element mold.

8. A dental crown according to claim 1, formed by compression molding.

9. A dental crown according to claim 1, formed by machining.

10. A permanent dental crown configured to be readily mounted in a patient's mouth as part of treatment of primary teeth and permanent molars,
   the dental crown consisting of a layer of acetal homopolymer resin,
   configured to define a tooth shaped top surface and depending flexible side surfaces extending continuously from the top surface towards a bottom portion of the dental crown,
   said layer of the acetal homopolymer resin being configured to provide dimensional stability and desired resilience of the crown, and
   at least one of said depending flexible continuous side surfaces being formed within the bottom portion of the crown with an undercut defining an inwardly directed inner surface of said bottom portion, the resilience of the flexible side surfaces and the undercut enabling the dental crown to be readily mountable on a primary tooth or permanent molar.

* * * * *